(12) United States Patent
Katayama et al.

(10) Patent No.: US 7,687,630 B2
(45) Date of Patent: Mar. 30, 2010

(54) METHOD FOR PRODUCING OPTICALLY ACTIVE QUINUCLIDINOLS HAVING ONE OR MORE SUBSTITUTED GROUPS AT THE 2-POSITION

(75) Inventors: Takeaki Katayama, Saitama (JP); Kunihiko Murata, Saitama (JP)

(73) Assignee: Kanto Kagaku Kabushiki Kaisha, Tokyo (JP)

( * ) Notice: Subject to any disclaimer, the term of this patent is extended or adjusted under 35 U.S.C. 154(b) by 94 days.

(21) Appl. No.: 11/906,103

(22) Filed: Sep. 28, 2007

(65) Prior Publication Data

US 2008/0081911 A1   Apr. 3, 2008

(30) Foreign Application Priority Data

Sep. 29, 2006   (JP) .............................. 2006-269642

(51) Int. Cl.
    *C07D 453/02* (2006.01)
(52) U.S. Cl. ..................................................... 546/137
(58) Field of Classification Search .................. 546/137
    See application file for complete search history.

(56) References Cited

U.S. PATENT DOCUMENTS

| 5,744,606 | A | 4/1998 | Brieden |
| 5,763,688 | A | 6/1998 | Ikariya et al. |
| 2002/0035147 | A1 | 3/2002 | Chappell et al. |
| 2003/0166978 | A1 | 9/2003 | Tsutsumi et al. |
| 2006/0047122 | A1* | 3/2006 | Takenaka ..................... 546/133 |

FOREIGN PATENT DOCUMENTS

| EP | 0 499 313 A1 | 8/1992 |
| EP | 0 829 480 A2 | 3/1998 |
| JP | 2500279 | 3/1996 |
| JP | 8-225466 A | 9/1996 |
| JP | 9-194480 A | 7/1997 |
| JP | 11-189600 A | 7/1999 |
| JP | 11-322649 A | 11/1999 |
| JP | 2000-256234 A | 9/2000 |
| JP | 2002-20287 A | 1/2002 |
| JP | 3273750 | 2/2002 |
| JP | 2002-531564 A | 9/2002 |
| JP | 2003-252884 A | 9/2003 |
| JP | 2003-277380 A | 10/2003 |
| JP | 2003277380 | * 10/2003 |
| JP | 2004-292434 A | 10/2004 |
| JP | 2005298411 | * 10/2005 |
| WO | WO 00/34276 A1 | 6/2000 |
| WO | WO 2004/078686 A1 | 9/2004 |

OTHER PUBLICATIONS

Gao, J-X et al., "A Ruthenium(II) Complex with a $C_2$-Symmetric Diphosphine/Diamine Tetradentate Ligand for Asymmetric Transfer Hydrogenation of Aromatic Ketones," *Organometallics* 1996; 15:1087-1089.

Mazurov, A. et al., "2-(Arylmethyl)-3-substituted quinuclidines as selective α-7 nicotinic receptor ligands," *Bioorg. & Med. Chem. Lett.* 2005; 15:2073-2077.

Murata, K. et al., "New Chiral Rhodium and Iridium Complexes with Chiral Diamine Ligands for Asymmetric Transfer Hydrogenation of Aromatic Ketones," *J. Org. Chem.* 1999; 64:2186-2187.

Swain, C.J. et al., "Quinuclidine Based NK-1 Antagonists 2: Determination of the Absolute Stereochemical Requirements," *Bioor. & Med. Chem. Lett*. 1993; 3(8):1703-1706.

Warawa, E.J. et al., "Quinuclidine Chemistry. 2. Synthesis and Antiinflammatory Properties of 2-Substituted Benzhydryl-3-quinuclidinols," *J. Med. Chem.* 1974; 17(5):497-501.

\* cited by examiner

*Primary Examiner*—D. Margaret Seaman
*Assistant Examiner*—Niloofar Rahmani
(74) *Attorney, Agent, or Firm*—Wolf, Greenfield & Sacks, P.C.

(57) ABSTRACT

The invention provides a method for producing optically active 3-quinuclidinols having one or more substituted groups at the 2-position; wherein 3-quinuclidinones having one or more substituted groups at the 2-position are reacted with compounds providing hydrogen in the presence of a certain metal complex.

14 Claims, No Drawings

METHOD FOR PRODUCING OPTICALLY ACTIVE QUINUCLIDINOLS HAVING ONE OR MORE SUBSTITUTED GROUPS AT THE 2-POSITION

FIELD OF THE INVENTION

The present invention relates to a method for producing optically active 3-quinuclidinols having one or more substituted groups at the 2-position, and particularly to a method for producing optically active cis-3-quinuclidinols having one or more substituted groups at the 2-position useful as optically and physiologically active compounds used in medicine and agrichemicals or as synthetic intermediates such as liquid crystal material.

BACKGROUND OF THE INVENTION

Many naturally occurring organic compounds have an optically active configuration. Among these, there are many organic compounds with physiological activity in which only one optical isomer has a desirable activity. Regarding the other optical isomer, which does not have a desirable activity, there are also known cases in which the optical isomer is not only devoid of a useful physiological activity for organisms, but in which it has even toxicity towards organisms. Therefore, as safe method for synthesizing pharmaceuticals and to produce a target compound or its intermediates, it is desirable to develop a method of synthesizing optically active compounds having a high optical purity.

Optically active alcohols are useful as an asymmetric source for synthesizing various optically active substances. Typically, optically active alcohols are produced by optical resolution of racemic compounds or by asymmetric synthesis using a biological catalyst or an asymmetric metal complex as a catalyst. In particular, the production of optically active alcohol by asymmetric synthesis is a technology which is recognized to be indispensable for producing optically active alcohols on a large scale.

Optically active quinuclidinols having one or more substituted groups at the 2-position, which are synthetic intermediates of optically and physiologically active compounds used for medicine, agrichemicals, etc., are one type of industrially useful optically active alcohols. For example, optically active 2-(3-pyridylmethyl)-3-quinuclidinol is a synthetic intermediate of nicotinic cholinergic receptor inhibiting substances which is useful in various therapies of disorders of the central nervous system (Patent Documents 1 and 2). Moreover, optically active 2-diphenylmethyl-3-quinuclidinol is a synthetic intermediate of a Substance P antagonist which is effective in therapies such as the treatment of disorders of the central nervous system and senile dementia of Alzheimer type (Patent Documents 3-6). Furthermore, a multitude of different physiological activities are reported for the compound in which the hydroxyl group at the 3-position is substituted by an amino group (Patent Document 7).

As mentioned hereinafter, methods for optically resolving racemic cis-quinuclidinol have been reported as method of producing optically active 3-quinuclidinol having one or more substituted groups at the 2-position. For example, according to Non-Patent Document 1, a method is known wherein the target substance is obtained by reacting racemic 2-arylmethyl-3-quinuclidinol with optically active 2-methoxy-2-phenylacetic acid to obtain diastereomers, followed by HPLC resolution and then hydrolysis; according to Non-Patent Document 2, a method is known wherein the target substance is obtained by reacting racemic 2-diarylmethyl-3-quinuclidinol with optically active mandelic acid for conversion into diastereomers, followed by resolution by recrystallization and then hydrolysis; according to Non-Patent Document 3, a method is known wherein the target substance is obtained by reacting racemic 2-diarylmethyl-3-quinuclidinol with optically active camphoric acid to obtain diastereomers, followed by resolution through recrystallization and then hydrolysis. However, these methods are complicated since they require the prior production of racemic quinuclidinol having one or more substituted groups at the 2-position and the conversion into diastereomers, which then needs to be followed by further processes such as resolution and deprotection.

Moreover, these methods are means for obtaining the target optical isomers by optical resolution of racemic 3-quinuclidinol having one or more substituted groups at the 2-position; since the other, non-target, optical isomer is left over, it is not possible to obtain a high yield. Consequently, it can hardly be said that these methods are simple and economic methods for producing optically active 3-quinuclidinol having one or more substituted groups at the 2-position.

On the other hand, a known method for obtaining optically active alcohol is the asymmetric hydrogenation of prochiral carbonyl compounds in the presence of an asymmetric metal complex catalyst. Patent Document 8 discloses a method for asymmetrically hydrogenating carbonyl compounds in the presence of a ruthenium metal complex having an optically active diphosphine compound such as BINAP, a base such as hydroxide of alkali earth metal, alkali metal, and an ethylenediamine-type optically active diamine compound. Patent Document 9 further discloses a method for hydrogenating carbonyl compounds using a ruthenium complex having optically active phosphine such as BINAP and an optically active 1,2-ethylenediamine-type ligand as catalyst. Patent Document 10 further discloses a method using a ruthenium complex having an optically active phosphine such as SKEWPHOS and an optically active 1,2-ethylenediamine-type ligand.

As method of synthesizing optically active 3-quinuclidinol using these asymmetric hydrogenation methods, Patent Document 11 mentions a method of hydrogenation of a quinuclidinone derivative selected from compounds consisting of 3-quinuclidinone, its adduct to a Lewis acid and the specific tertiary and quaternary salts corresponding thereto in the presence of a rhodium, iridium or ruthenium complex having a chiral diphosphine. Patent Document 12 discloses a method for producing optically active 3-quinuclidinol by hydrogenating 3-quinuclidinone in the presence of a base and an optically active ruthenium complex having an optically active bidentate ligand and an optically active 1,2-ethylenediamine-type ligand. Patent Document 13 further discloses a method for hydrogenating 3-quinuclidinone by using, as catalyst, a rhodium complex having an optically active phosphine having a ferrocene skeleton and a 1,2-ethylenediamine-type ligand. In this Patent Document, even though prochiral ring ketones which may have a substitution group such as 3-quinuclidinone is described, no specific examples of 3-quinuclidinone having a substitution group at the 2-position is described. In other words, these documents all report how to obtain 3-quinuclidinol by reduction of 3-quinuclidinone not having a substitution group at the 2-position, without any mention whatsoever of an example of synthesizing optically active 3-quinuclidinol having a substitution group at the 2-position from a racemic 3-quinuclidinone having a substitution group at the 2-position.

Moreover, regarding catalytic asymmetric hydrogenation, methods using alcohol and formic acid as reducing agent, i.e.

catalytic asymmetric reduction reaction, are also frequently reported. In particular, the properties of an asymmetric ruthenium catalyst having an amine ligand with a sulfonylamide group as anchor (Patent Document 14) ought to be specifically mentioned. Apart from this, a similar catalytic system with a ruthenium-amine complex as basic skeleton is also reported (Non-Patent Document 4). Moreover, in the same way, rhodium and iridium catalysts with a metal-amine bond are also reported (Non-Patent Document 5). However, these documents report no example of synthesizing optically active 3-quinuclidinol having one or more substituted groups at the 2-position by asymmetric reduction of 3-quinuclidinone having one or more substituted groups at the 2-position or even a method for synthesizing optically active 3-quinuclidinol by asymmetric reduction of 3-quinuclidinone not having one or more substituted groups.

Further, regarding asymmetric reduction accompanying dynamic kinetic resolution, Patent Document 15 reports synthesis of optically active hydrobenzoin from racemic benzoin, but does not report an example of reaction by synthesizing optically active 3-quinuclidinol from racemic 3-quinuclidinone having a substitution group at the 2-position.

As shown above, a method for synthesizing optically active 3-quinuclidinol having one or more substituted groups at the 2-position by asymmetric reduction of quinuclidinone having one or more substituted groups at the 2-position and by using a reduction technique has not hitherto been known.

Patent Document 1: JP, A, 2002-531564
Patent Document 2: WO 2000-0034276
Patent Document 3: Japanese Patent No. 3273750
Patent Document 4: European Patent No. 829480
Patent Document 5: Japanese Patent No. 2500279
Patent Document 6: European Patent No. 499313
Patent Document 7: JP, A, 2002-020287
Patent Document 8: JP, A, 8-225466
Patent Document 9: JP, A, 11-189600
Patent Document 10: JP, A, 2003-252884
Patent Document 11: JP, A, 9-194480
Patent Document 12: JP, A, 2003-277380
Patent Document 13: JP, A, 2004-292434
Patent Document 14: JP, A, 11-322649
Patent Document 15: Japanese Patent No. 3630002
Non-Patent Document 1: Bioorg & Med. Chem. Lett. 15, 2073-2077 (2005)
Non-Patent Document 2: J. Med. Chem. 17, 497-501 (1974)
Non-Patent Document 3: Bioorg & Med. Chem. Lett. 8, 1703-1706 (1993)
Non-Patent Document 4: Organometallics 1996, 15, 1087.
Non-Patent Document 5: J. Org. Chem. 1999, 64, 2186.

SUMMARY OF THE INVENTION

The present invention provides an efficient method for producing optically active quinuclidinols having one or more substituted groups at the 2-position, which hitherto could only be obtained by an optical resolution method, from quinuclidinone having one or more substituted groups at the 2-position by using, as catalyst, ruthenium, rhodium or iridium complexes with optically active diamine compounds as ligands; in particular, the present invention provides an efficient method for producing cis-3-quinuclidinols having one or more substituted groups at the 2-position.

The present inventors, as a result of extensive studies of efficient methods for producing optically active quinuclidinols having one or more substituted groups at the 2-position, discovered that ruthenium, rhodium or iridium complex catalysts having a sulfonyldiamine ligand have excellent properties as asymmetric reduction catalysts of 3-quinuclidinones having one or more substituted groups at the 2-position, further discovered that, when racemic quinuclidinones having one or more substituted groups at the 2-position are reduced, accompanied by dynamic kinetic resolution, and the configuration of the asymmetric carbon is simultaneously controlled in two places, a high yield of optically active cis-3-quinuclidinols having one or more substituted groups at the 2-position can be efficiently obtained, and thus completed the invention.

In other words, the present invention relates to a method for producing optically active 3-quinuclidinols having one or more substituted groups at the 2-position; characterized in that 3-quinuclidinones having one or more substituted groups at the 2-position are reacted with compounds providing hydrogen in the presence of a metal complex represented by the general formula (1)

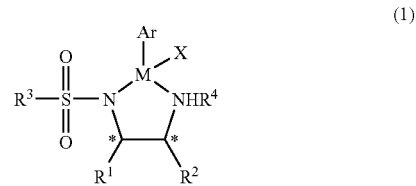

(1)

(wherein, $R^1$ and $R^2$ are both simultaneously or each independently alkyl groups, phenyl groups, naphthyl groups or cycloalkyl groups which may have one or more substituted groups, optionally, $R^1$ and $R^2$ may also join to form an alicyclic ring, $R^3$ is an alkyl group, perfluoroalkyl group, naphthyl group, phenyl group or camphor which may have one or more substituted groups, $R^4$ is a hydrogen atom or an alkyl group, Ar, joined to M via a π bond, is a benzene ring which may have one or more substituted groups or a cyclopentadienyl group which may have one or more substituted groups, X is a hydride group or an anionic group, M is ruthenium, rhodium or iridium, * represents an asymmetric carbon atom).

The invention also relates to a method for producing optically active 3-quinuclidinols having one or more substituted groups at the 2-position; characterized in that 3-quinuclidinones having one or more substituted groups at the 2-position are reacted with compounds providing hydrogen in the presence of a metal complex represented by the general formula (2)

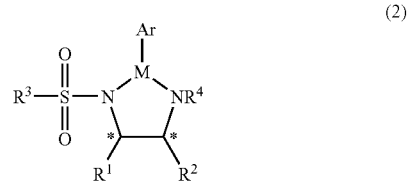

(2)

(wherein, $R^1$, $R^2$, $R^3$, $R^4$, Ar, M and * each have the same meaning as in Claim 1).

The invention further relates to the above-mentioned methods wherein in general formula (1) or general formula (2), M is ruthenium.

The invention also relates to the above-mentioned methods wherein in general formula (1) or general formula (2), M is iridium.

The invention further relates to the above-mentioned methods wherein in general formula (1) or general formula (2), M is rhodium.

The invention also relates to the above-mentioned methods characterized in that the optically active 3-quinuclidinols having one or more substituted groups at the 2-position are obtained diastereoselectively and enantioselectively.

The invention further relates to the above-mentioned methods; wherein the 3-quinuclidinones having one or more substituted groups at the 2-position are the compounds expressed by general formula (3) hereinafter, the compounds expressed by general formula (4) hereinafter, or a mixture, at any ratio, of the compounds expressed by general formula (3) and the compounds expressed by general formula (4), and the optically active 3-quinuclidinols having one or more substituted groups at the 2-position that are to be produced are the optically active cis-3-quinuclidinols having $R^5$ at the 2-position represented by general formula (5) or general formula (6) hereinafter.

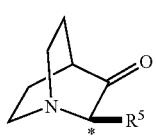

(3)

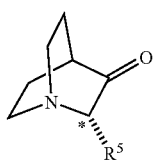

(4)

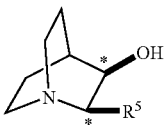

(5)

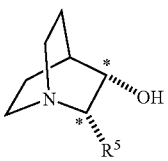

(6)

(wherein, $R^5$ represents an alkyl group with a carbon number of 1 to 20, which may be substituted by an aromatic ring and which may include a heteroatom, * represents an asymmetric carbon atom).

The invention also relates to the above-mentioned methods wherein, in general formulae (3)-(6), $R^5$ is a diphenylmethyl group, a 3-pyridylmethyl group or a benzyl group, which may have one or more substituted groups.

The invention further relates to the use of the metal complexes represented by general formula (1) or general formula (2) for producing optically active 3-quinuclidinols having one or more substituted groups at the 2-position.

DETAILED DESCRIPTION

The invention is based on the discovery showing that the high stereoselectivity, which cannot be obtained when 3-quinuclidinones not substituted at the 2-position are used as substrate, is obtained when the metal complexes expressed by general formula (1) or general formula (2) are used for obtaining 3-quinuclidinols from 3-quinuclidinones having one or more substituted groups at the 2-position by reduction reaction. This is because these 3-quinuclidinones having one or more substituted groups at the 2-position are subjected to asymmetric reduction, accompanied by dynamic kinetic resolution; thus it is possible to control the asymmetric points of two places. In particular, optically active cis-quinuclidinols having one or more substituted groups at the 2-position can very efficiently be produced. As shown above, according to the present invention, 3-quinuclidinols having one or more substituted groups at the 2-position can be obtained with a high reaction yield as well as a high diastereoselectivity and optical purity.

In the metal complex catalysts of the present invention, examples for $R^1$ and $R^2$ in general formula (1) and general formula (2) include alkyl groups which may have one or more substituted groups, for example, alkyl groups with a carbon number of 1 to 10 such as methyl group, ethyl group, n-propyl group, isopropyl group, n-butyl group, sec-butyl group, tert-butyl group, phenyl groups which may have one or more substituted groups, for example, phenyl groups having an alkyl group with a carbon number of 1 to 5 such as phenyl group, 4-methylphenyl group, 3,5-dimethylphenyl group, phenyl groups having a halogen substituted group such as 4-fluorophenyl group, 4-chlorophenyl group, phenyl groups having an alkoxy group such as 4-methoxyphenyl, naphthyl groups which may have one or more substituted groups, for example, naphthyl group, 5,6,7,8-tetrahydro-1-naphthyl group, 5,6,7,8-tetrahydro-2-naphthyl group, cycloalkyl groups which may have one or more substituted groups, for example, cyclopentyl group, cyclohexyl group. Optionally, $R^1$ and $R^2$ may also join to form an alicyclic ring having an unsubstituted or one or more substituted groups. For example, $R^1$ and $R^2$ may also join to form a ring such as a cyclopentane ring or a cyclohexane ring. It is preferred that $R^1$ and $R^2$ are both phenyl groups or that $R^1$ and $R^2$ join to form a cyclohexane ring.

Examples of the alkyl group of $R^3$ in general formula (1) and general formula (2) include, for example, alkyl groups with a carbon number of 1 to 10 such as methyl group, ethyl group, n-propyl group, isopropyl group, n-butyl group, sec-butyl group, tert-butyl group. These alkyl groups may have one or more substituted groups, for example, they may have one or more substituted groups of one or more fluorine atoms. Examples of alkyl groups comprising one or more fluorine atoms include, for example, fluoromethyl group, difluoromethyl group, trifluoromethyl group, pentafluoroethyl group. Further, examples of naphthyl groups which may have one or more substituted groups include, for example, unsubstituted naphthyl group, 5,6,7,8-tetrahydro-1-naphthyl group, 5,6,7, 8-tetrahydro-2-naphthyl group. Moreover, examples of phenyl groups which may have one or more substituted groups include, for example, unsubstituted phenyl group, phenyl groups having an alkyl group such as 4-methylphenyl group, 3,5-dimethylphenyl group, 2,4,6-trimethylphenyl group, 2,4, 6-triisopropylphenyl group, phenyl groups having a halogen-substituted group such as 4-fluorophenyl group, 4-chlorophenyl group, phenyl groups having an alkoxy group such as 4-methoxyphenyl group.

Specific examples for $R^4$ in general formula (1) and general formula (2) include alkyl groups with a carbon number of 1 to 5 such as methyl group, ethyl group, and a hydrogen atom; preferred is a hydrogen atom. Examples of Ar in general formula (1) and general formula (2) are benzene-ring groups or cyclopentadienyl groups, which may have one or more substituted groups. Examples of benzene rings include, for example, apart from unsubstituted benzene, benzene having an alkyl group such as toluene, o-, m- or p-xylene, o-, m-, or p-cymene, 1,2,3-, 1,2,4- or 1,3,5-trimethylbenzene, 1,2,4,5-tetramethylbenzene, 1,2,3,4-tetramethylbenzene, pentamethylbenzene, hexamethylbenzene. Further, examples of cyclopentadienyl groups which may have one or more substituted groups include cyclopentadienyl group, methylcyclopentadienyl group, 1,2-dimethylcyclopentadienyl group, 1,3-dimethylcyclopentadienyl group, 1,2,3-trimethylcyclopentadienyl group, 1,2,4-trimethylcyclopentadienyl group, 1,2,3,4-tetramethylcyclopentadienyl group, 1,2,3,4,5-pentamethylcyclopentadienyl group.

M in general formula (1) and general formula (2) is any one of ruthenium, rhodium and iridium. X in general formula (1) is a hydride group or an anionic group, examples include, for example, hydride group, μ-oxo group, fluorine group, chlorine group, bromine group, iodine group, tetrafluoroborate group, tetrahydroborate group, tetrakis [3,5-bis(trifluoromethyl)phenyl]borate group, acetoxy group, benzoyloxy group, (2,6-dihydroxybenzoyl)oxy group, (2,5-dihydroxybenzoyl)oxy group, (3-aminobenzoyl)oxy group, (2,6-methoxybenzoyl)oxy group, (2,4,6-triisopropylbenzoyl)oxy group, 1-naphthalenecarboxylic acid group, 2-naphthalenecarboxylic acid group, trifluoroacetoxy group, trifluoromethanesulfonimide group, nitromethyl group, nitroethyl group, hydroxide group. X is preferably a hydride group, a hydroxide group, a bridged oxy group, a fluorine group, a chlorine group, a bromine group or a iodine group.

The metal catalysts represented by general formula (1) and general formula (2) have a structure wherein a bidentate ligand of sulfonylethylenediamine compounds $(R^3SO_2NHCHR^1CHR^2NHR^4)$ is joined to the metal. Specific examples of sulfonylethylenediamine compounds include N-(p-toluenesulfonyl)-1,2-diphenylethylenediamine (TsDPEN), N-methanesulfonyl-1,2-diphenylethylenediamine (MsDPEN), N-methyl-N'-(p-toluenesulfonyl)-1,2-diphenylethylenediamine, N-(p-methoxyphenylsulfonyl)-1,2-diphenylethylenediamine, N-(p-chlorophenylsulfonyl)-1,2-diphenylethylenediamine, N-trifluoromethanesulfonyl-1,2-diphenylethylenediamine, N-(2,4,6-trimethylbenzenesulfonyl)-1,2-diphenylethylenediamine, N-(2,4,6-triisopropylbenzenesulfonyl)-1,2-diphenylethylenediamine, N-(4-tert-butylbenzenesulfonyl)-1,2-diphenylethylenediamine, N-(2-naphthylsulfonyl)-1,2-diphenylethylenediamine, N-(3,5-dimethylbenzenesulfonyl)-1,2-diphenylethylenediamine, N-pentamethylbenzenesulfonyl-1,2-diphenylethylenediamine, and 1,2-N-tosylcyclohexanediamine (TsCYDN). Among these, TsDPEN and TsCYDN are preferred.

Regarding the method of preparing the metal complex catalysts represented by general formula (1) and general formula (2), the descriptions of Angew. Chem., Int. Ed. Engl. Vol. 36, p. 285 (1997) and J. Org. Chem. Vol. 64, p. 2186 (1999) can be consulted. Specifically, synthesis is possible by reacting a transition metal complex such as ruthenium-arene complexes, pentamethylcyclopentadienyl-rhodium complexes, pentamethylcyclopentadienyl-iridium complexes with a sulfonyldiamine ligand.

Further, one or more organic compounds, which are used as reagents in the synthesis of the ruthenium complexes expressed by general formula (1) and general formula (2), may be included in the ruthenium complexes expressed by general formula (1) and general formula (2). Examples of organic compounds, which signify organic coordinating solvents in this context, include, for example, aromatic hydrocarbon solvents such as toluene, xylene, aliphatic hydrocarbon solvents such as pentane, hexane, halogenated hydrocarbon solvents such as methylene chloride, ether-based solvents such as ether, tetrahydrofuran, alcohol-based solvents such as methanol, ethanol, 2-propanol, butanol, benzylalcohol, ketone-based solvents such as acetone, methylethylketone, cyclohexylketone, organic solvents including a heteroatom such as acetonitrile, DMF, N-methylpyrrolidone, DMSO, triethylamine. Quinuclidinones having one or more substituted groups at the 2-position used in the hydrogenation reaction such as

[1] quinuclidinone derivatives having one or more substituted groups only at the 2-position:
2-pyridylmethyl-3-quinuclidinone, 2-diphenylmethyl-3-quinuclidinone, 2-di(4-fluorophenyl)methyl-3-quinuclidinone, 2-methyl-3-quinuclidinone, 2,2-dimethyl-3-quinuclidinone, 2-ethyl-3-quinuclidinone, 2,2-diethyl-3-quinuclidinone, 2-n-propyl-3-quinuclidinone, 2,2-di-n-propyl-3-quinuclidinone, 2-i-propyl-3-quinuclidinone, 2,2-di-i-propyl-3-quinuclidinone, 2-butyl-3-quinuclidinone, 2,2-dibutyl-3-quinuclidinone, 2-t-butyl-3-quinuclidinone, and 2-benzyl-3-quinuclidinone,

[2] quinuclidinone derivatives having one or more substituted groups at the 2-position and at the 4-position:
2-methyl-4-methyl-3-quinuclidinone, 2-methyl-4-ethyl-3-quinuclidinone, 2-methyl-4-n-propyl-3-quinuclidinone, 2-methyl-4-i-propyl-3-quinuclidinone, 2-methyl-4-butyl-3-quinuclidinone, 2-methyl-4-t-butyl-3-quinuclidinone, 2-methyl-4-benzyl-3-quinuclidinone, 2-benzyl-4-methyl-3-quinuclidinone, 2-benzyl-4-ethyl-3-quinuclidinone, 2-benzyl-4-n-propyl-3-quinuclidinone, 2-benzyl-4-i-propyl-3-quinuclidinone, 2-benzyl-4-butyl-3-quinuclidinone, 2-benzyl-4-t-butyl-3-quinuclidinone, 2-benzyl-4-benzyl-3-quinuclidinone, 2-diphenylmethyl-4-methyl-3-quinuclidinone, 2-diphenylmethyl-4-ethyl-3-quinuclidinone, 2-diphenylmethyl-4-n-propyl-3-quinuclidinone, 2-diphenylmethyl-4-i-propyl-3-quinuclidinone, 2-diphenylmethyl-4-butyl-3-quinuclidinone, 2-diphenylmethyl-4-t-butyl-3-quinuclidinone, 2-diphenylmethyl-4-benzyl-3-quinuclidinone, 2-pyridylmethyl-4-methyl-3-quinuclidinone, 2-pyridylmethyl-4-ethyl-3-quinuclidinone, 2-pyridylmethyl-4-n-propyl-3-quinuclidinone, 2-pyridylmethyl-4-i-propyl-3-quinuclidinone, 2-pyridylmethyl-4-butyl-3-quinuclidinone, 2-pyridylmethyl-4-t-butyl-3-quinuclidinone, 2-pyridylmethyl-4-benzyl-3-quinuclidinone,

[3] quinuclidinone derivatives having one or more substituted groups at the 2-position and at the 5-position:
2-methyl-5-methyl-3-quinuclidinone, 2-methyl-5,5-dimethyl-3-quinuclidinone, 2-methyl-5-ethyl-3-quinuclidinone, 2-methyl-5,5-diethyl-3-quinuclidinone, 2-methyl-5-n-propyl-3-quinuclidinone, 2-methyl-5,5-di-n-propyl-3-quinuclidinone, 2-methyl-5-i-propyl-3-quinuclidinone, 2-methyl-5,5-di-i-propyl-3-quinuclidinone, 2-methyl-5-butyl-3-quinuclidinone, 2-methyl-5,5-dibutyl-3-quinuclidinone, 2-methyl-5-t-butyl-3-quinuclidinone, 2-methyl-5-benzyl-3-quinuclidinone, 2-benzyl-5-methyl-3-quinuclidinone, 2-benzyl-5,5-dimethyl-3-quinuclidinone, 2-benzyl-5-ethyl-3-quinuclidinone, 2-benzyl-5,5-diethyl-3-quinuclidinone, 2-benzyl-5-n-propyl-3-quinuclidinone, 2-benzyl-S,S-di-n-propyl-3-quinuclidinone, 2-benzyl-S-i-propyl-3-quinuclidinone, 2-benzyl-5,5-di-i-propyl-3-quinuclidinone, 2-benzyl-5-butyl-3-quinuclidinone, 2-benzyl-5,5-dibutyl-3-quinuclidinone, 2-benzyl-5-t-butyl-3-quinuclidinone, 2-benzyl-5-benzyl-3-quinuclidinone, 2-diphenylmethyl-5-methyl-3-quinuclidinone, 2-diphenylmethyl-5,5-dimethyl-3-quinuclidinone, 2-diphenylmethyl-5-ethyl-3-quinuclidinone, 2-diphenylmethyl-5,5-diethyl-3-quinuclidinone, 2-diphenylmethyl-5-n-propyl-3-quinuclidinone, 2-diphenylmethyl-5,5-di-n-propyl-3-quinuclidinone, 2-diphenylmethyl-5-i-propyl-3-quinuclidinone, 2-diphenylmethyl-5,5-di-i-propyl-3-quinuclidinone, 2-diphenylmethyl-5-butyl-3-quinuclidinone, 2-diphenylmethyl-5,5-dibutyl-3-quinuclidinone, 2-diphenylmethyl-5-t-butyl-3-quinuclidinone, 2-diphenylmethyl-5-benzyl-3-quinuclidinone, 2-pyridylmethyl-5-methyl-3-quinuclidinone, 2-pyridylmethyl-5,5-dimethyl-3-quinuclidinone, 2-pyridylmethyl-5-ethyl-3-quinuclidinone, 2-pyridylmethyl-5,5-diethyl-3-quinuclidinone, 2-pyridylmethyl-5-n-propyl-3-quinuclidinone, 2-pyridylmethyl-5,5-di-n-propyl-3-quinuclidinone, 2-pyridylmethyl-5-i-propyl-3-quinuclidinone, 2-pyridylmethyl-5,5-di-i-propyl-3-quinuclidinone, 2-pyridylmethyl-5-butyl-3-quinuclidinone, 2-pyridylmethyl-5,5-dibutyl-3-quinuclidinone, 2-pyridylmethyl-5-t-butyl-3-quinuclidinone, 2-pyridylmethyl-5-benzyl-3-quinuclidinone,

[4] quinuclidinone derivatives having one or more substituted groups at the 2-position and at the 6-position:
2-methyl-6-methyl-3-quinuclidinone, 2-methyl-6,6-dimethyl-3-quinuclidinone, 2-methyl-6-ethyl-3-quinuclidinone, 2-methyl-6,6-diethyl-3-quinuclidinone, 2-methyl-6-n-propyl-3-quinuclidinone, 2-methyl-6,6-di-n-propyl-3-quinuclidinone, 2-methyl-6-i-propyl-3-quinuclidinone, 2-methyl-6,6-di-i-propyl-3-quinuclidinone, 2-methyl-6-butyl-3-quinuclidinone, 2-methyl-6,6-dibutyl-3-quinuclidinone, 2-methyl-6-t-butyl-3-quinuclidinone, 2-methyl-6-benzyl-3-quinuclidinone, 2-benzyl-6-methyl-3-quinuclidinone, 2-benzyl-6,6-dimethyl-3-quinuclidinone, 2-benzyl-6-ethyl-3-quinuclidinone, 2-benzyl-6,6-diethyl-3-quinuclidinone, 2-benzyl-6-n-propyl-3-quinuclidinone, 2-benzyl-6,6-di-n-propyl-3-quinuclidinone, 2-benzyl-6-i-propyl-3-quinuclidinone, 2-benzyl-6,6-di-i-propyl-3-quinuclidinone, 2-benzyl-6-butyl-3-quinuclidinone, 2-benzyl-6,6-dibutyl-3-quinuclidinone, 2-benzyl-6-t-butyl-3-quinuclidinone, 2-benzyl-6-benzyl-3-quinuclidinone, 2-diphenylmethyl-6-methyl-3-quinuclidinone, 2-diphenylmethyl-6,6-dimethyl-3-quinuclidinone, 2-diphenylmethyl-6-ethyl-3-quinuclidinone, 2-diphenylmethyl-6,6-diethyl-3-quinuclidinone, 2-diphenylmethyl-6-n-propyl-3-quinuclidinone, 2-diphenylmethyl-6,6-di-n-propyl-3-quinuclidinone, 2-diphenylmethyl-6-i-propyl-3-quinuclidinone, 2-diphenylmethyl-6,6-di-i-propyl-3-quinuclidinone, 2-diphenylmethyl-6-butyl-3-quinuclidinone, 2-diphenylmethyl-6,6-dibutyl-3-quinuclidinone, 2-diphenylmethyl-6-t-butyl-3-quinuclidinone, 2-diphenylmethyl-6-benzyl-3-quinuclidinone, 2-pyridylmethyl-6-methyl-3-quinuclidinone, 2-pyridylmethyl-6,6-dimethyl-3-quinuclidinone, 2-pyridylmethyl-6-ethyl-3-quinuclidinone, 2-pyridylmethyl-6,6-diethyl-3-quinuclidinone, 2-pyridylmethyl-6-n-propyl-3-quinuclidinone, 2-pyridylmethyl-6,6-di-n-propyl-3-quinuclidinone, 2-pyridylmethyl-6-i-propyl-3-quinuclidinone, 2-pyridylmethyl-6,6-di-i-propyl-3-quinuclidinone, 2-pyridylmethyl-6-butyl-3-quinuclidinone, 2-pyridylmethyl-6,6-dibutyl-3-quinuclidinone, 2-pyridylmethyl-6-t-butyl-3-quinuclidinone, 2-pyridylmethyl-6-benzyl-3-quinuclidinone,

[5] quinuclidinone derivatives having one or more substituted groups at the 2-position and at the 7-position:
2-methyl-7-methyl-3-quinuclidinone, 2-methyl-7,7-dimethyl-3-quinuclidinone, 2-methyl-7-ethyl-3-quinuclidinone, 2-methyl-7,7-diethyl-3-quinuclidinone, 2-methyl-7-n-propyl-3-quinuclidinone, 2-methyl-7,7-di-n-propyl-3-quinuclidinone, 2-methyl-7-i-propyl-3-quinuclidinone, 2-methyl-7,7-di-i-propyl-3-quinuclidinone, 2-methyl-7-butyl-3-quinuclidinone, 2-methyl-7,7-dibutyl-3-quinuclidinone, 2-methyl-7-t-butyl-3-quinuclidinone, 2-methyl-7-benzyl-3-quinuclidinone, 2-benzyl-7-methyl-3-quinuclidinone, 2-benzyl-7,7-dimethyl-3-quinuclidinone, 2-benzyl-7-ethyl-3-quinuclidinone, 2-benzyl-7,7-diethyl-3-quinuclidinone, 2-benzyl-7-n-propyl-3-quinuclidinone, 2-benzyl-7,7-di-n-propyl-3-quinuclidinone, 2-benzyl-7-i-propyl-3-quinuclidinone, 2-benzyl-7,7-di-i-propyl-3-quinuclidinone, 2-benzyl-7-butyl-3-quinuclidinone, 2-benzyl-7,7-dibutyl-3-quinuclidinone, 2-benzyl-7-t-butyl-3-quinuclidinone, 2-benzyl-7-benzyl-3-quinuclidinone, 2-diphenylmethyl-7-methyl-3-quinuclidinone, 2-diphenylmethyl-7,7-dimethyl-3-quinuclidinone, 2-diphenylmethyl-7-ethyl-3-quinuclidinone, 2-diphenylmethyl-7,7-diethyl-3-quinuclidinone, 2-diphenylmethyl-7-n-propyl-3-quinuclidinone, 2-diphenylmethyl-7,7-di-n-propyl-3-quinuclidinone, 2-diphenylmethyl-7-i-propyl-3-quinuclidinone, 2-diphenylmethyl-7,7-di-i-propyl-3-quinuclidinone, 2-diphenylmethyl-7-butyl-3-quinuclidinone, 2-diphenylmethyl-7,7-dibutyl-3-quinuclidinone, 2-diphenylmethyl-7-t-butyl-3-quinuclidinone, 2-diphenylmethyl-7-benzyl-3-quinuclidinone, 2-pyridylmethyl-7-methyl-3-quinuclidinone, 2-pyridylmethyl-7,7-dimethyl-3-quinuclidinone, 2-pyridylmethyl-7-ethyl-3-quinuclidinone, 2-pyridylmethyl-7,7-diethyl-3-quinuclidinone, 2-pyridylmethyl-7-n-propyl-3-quinuclidinone, 2-pyridylmethyl-7,7-di-n-propyl-3-quinuclidinone, 2-pyridylmethyl-7-i-propyl-3-quinuclidinone, 2-pyridylmethyl-7,7-di-i-propyl-3-quinuclidinone, 2-pyridylmethyl-7-butyl-3-quinuclidinone, 2-pyridylmethyl-7,7-dibutyl-3-quinuclidinone, 2-pyridylmethyl-7-t-butyl-3-quinuclidinone, 2-pyridylmethyl-7-benzyl-3-quinuclidinone,

[6] quinuclidinone derivatives having one or more substituted groups at the 2-position and at the 8-position:
2-methyl-8-methyl-3-quinuclidinone, 2-methyl-8,8-dimethyl-3-quinuclidinone, 2-methyl-8-ethyl-3-quinuclidinone, 2-methyl-8,8-diethyl-3-quinuclidinone, 2-methyl-8-n-propyl-3-quinuclidinone, 2-methyl-8,8-di-n-propyl-3-quinuclidinone, 2-methyl-8-i-propyl-3-quinuclidinone, 2-methyl-8,8-di-i-propyl-3-quinuclidinone, 2-methyl-8-butyl-3-quinuclidinone, 2-methyl-8,8-dibutyl-3-quinuclidinone, 2-methyl-8-t-butyl-3-quinuclidinone, 2-methyl-8-benzyl-3-quinuclidinone, 2-benzyl-8-methyl-3-quinuclidinone, 2-benzyl-8,8-dimethyl-3-quinuclidinone, 2-benzyl-8-ethyl-3-quinuclidinone, 2-benzyl-8,8-diethyl-3-quinuclidinone, 2-benzyl-8-n-propyl-3-quinuclidinone, 2-benzyl-8,8-n-propyl-3-quinuclidinone, 2-benzyl-8-i-propyl-3-quinuclidinone, 2-benzyl-8,8-i-propyl-3-quinuclidinone, 2-benzyl-8-butyl-3-quinuclidinone, 2-benzyl-8,8-dibutyl-3-quinuclidinone, 2-benzyl-8-t-butyl-3-quinuclidinone, 2,8-dibenzyl-3-quinuclidinone, 2-diphenylmethyl-8-methyl-3-quinuclidinone, 2-diphenylmethyl-8,8-dimethyl-3-quinuclidinone, 2-diphenylmethyl-8-ethyl-3-quinuclidinone, 2-diphenylmethyl-8,8-diethyl-3-quinuclidinone, 2-diphenylmethyl-8-n-propyl-3-quinuclidinone, 2-diphenylmethyl-di-8,8-n-propyl-3-quinuclidinone, 2-diphenylmethyl-8-i-propyl-3-quinuclidinone, 2-diphenylmethyl-8,8-di-i-propyl-3-quinuclidinone, 2-diphenylmethyl-8-butyl-3-quinuclidinone, 2-diphenylmethyl-8,8-dibutyl-3-quinuclidinone, 2-diphenylmethyl-8-t-butyl-3-quinuclidinone, 2-diphenylmethyl-8-benzyl-3-quinuclidinone, 2-pyridylmethyl-8-methyl-3-quinuclidinone, 2-pyridylmethyl-8,8-dimethyl-3-quinuclidinone, 2-pyridylmethyl-8-ethyl-3-quinuclidinone, 2-pyridylmethyl-8,8-diethyl-3-quinuclidinone, 2-pyridylmethyl-8-n-propyl-3-quinuclidinone, 2-pyridylmethyl-8,8-di-n-propyl-3-quinuclidinone, 2-pyridylmethyl-8-i-propyl-3-quinuclidinone, 2-pyridylmethyl-8,8-di-i-propyl-3-quinuclidinone, 2-pyridylmethyl-8-butyl-3-quinuclidinone, 2-pyridylmethyl-8,8-dibutyl-3-quinuclidinone, 2-pyridylmethyl-8-t-butyl-3-quinuclidinone, 2-pyridylmethyl-8-benzyl-3-quinuclidinone, further, quinuclidinone derivatives having one or more substituted groups in multiple positions including the 2-position and other positions, can be used as ketone substrate. The number of substituted groups is one for each concerned carbon atom, when the substituted groups are at the 2- and 4-position, one or two for each concerned carbon atom, when the substituted groups are at the 5-, 6-, 7- and 8-position. For the whole quinuclidinone the number of substituted groups may be from 1 to 10.

According to the present invention, alcohol is produced, for example, by introducing the metal complex catalysts represented by general formula (1) or general formula (2) and ketone compounds into a solvent, by mixing this in the presence of a hydrogen donor and by reduction of the ketone. The amount of catalyst used, expressed as the S/C (S: substrate, C: catalyst) molar ratio of substrate to metal catalyst, is not particularly limited, however, a ratio in the range of 10 to 100,000 can be used; when considering practicality, a range of 50 to 10,000 is preferred.

According to the present invention, it is possible to use an ordinary hydrogen donor as reaction solvent or, in order to increase the solubility of the source material, an alcohol-based solvent such as methanol, ethanol, 2-propanol, 2-methyl-2-propanol, 2-methyl-2-butanol, an ether-based solvent such as tetrahydrofuran (THF), diethylether, a solvent including a heteroatom such as acetonitrile, DMSO, DMF, an aromatic hydrocarbon solvent such as toluene, xylene, an aliphatic hydrocarbon solvent such as pentane, hexane, a halogenated hydrocarbon solvent such as methylene chloride, other solvents such as water used on their own or together with other solvents. Moreover, it is also possible to use a mixed solvent of the above-listed examples of solvents with other non-listed solvents. In particular, DMF and methylene chloride can be advantageously used.

In the present invention, any source capable of donating hydrogen to a carbonyl group may be used as hydrogen donor, examples include alcohol compounds having a hydrogen atom at the α-position such as methanol, ethanol, 1-propanol, 2-propanol, 1-butanol, sec-butylalcohol, benzylalcohol, formic acid and formates such as sodium, potassium.

The amount of hydrogen donor is expressed in relation to the amount of substrate used, typically, 1 mol time to an excessively large amount such as 1000 mol times may be used; when alcohol is used as hydrogen donor, an excessively large amount is used to prevent isomerization by reverse reaction; when formic acid is used as hydrogen donor, it can be used in the range from 1 to 20 mol times, and preferably in the range from 2 to 10 mol times.

In the production method according to the present invention it is preferred to add a base for bringing out the function of the metal complex catalyst and for obtaining the target substance with a high optical purity by dynamic kinetic resolution. Examples of bases that can be used include alkali metal hydroxides such as lithium hydroxide, sodium hydroxide, potassium hydroxide, alkali metal alkoxides such as lithium methoxide, sodium methoxide, sodium ethoxide, potassium isopropoxide organic amines such as trimethylamine, triethylamine, triisopropylamine. Preferred are sodium hydroxide, potassium hydroxide or triethylamine as Tertiar,™ amine. These bases may be used on their own or two or more bases may be used together.

Regarding the amount of base, it is possible to use an excessive amount in relation to the metal complex catalyst such as, for example, a mol ratio of 1 to 1000; however, a mol ratio of 1 to 100 is preferred. In general, when using alcohol as hydrogen donor, the preferred amount of base, expressed as potassium hydroxide, is a mol ratio of 1 to 10; an excessive amount is not preferred. When using formic acid as hydrogen donor, the preferred amount of base is a mol ratio of 1 to 10 of triethylamine to catalyst; an excessive amount, for example a mol ratio of 1 to 1000, may also be used.

Regarding the metal complex catalysts in the present invention, when using the chloride complex expressed by general formula (1) in which X is Cl, it is necessary to add a base so as to bring out the function of the metal complex catalyst. Examples of preferred combinations of bases and hydrogen donors include 2-propanol/potassium hydroxide or sodium hydroxide, formic acid/triethylamine.

For performing an efficient reduction reaction, the combination of formic acid and triethylamine is most preferred.

Further, when the metal complex catalyst, among the compounds expressed by general formula (1), is a compound in which X is a hydride group, and when a metal amide complex expressed by general formula (2) is used, reaction can be performed even without the presence of a base. Therefore, when the substrate of 3-quinuclidinones having one or more substituted groups at the 2-position is particularly unstable in a base, it is preferred to perform the reaction in the absence of a base.

The base may be mixed by preparing beforehand a mixture with the solvent and the hydrogen donor; however, the base may also be added inside the reaction vessel. When using a combination of formic acid and organic amine, a mixture of formic acid and organic amine may be prepared beforehand; however, the mixture may also be prepared inside the reaction vessel. When using formic acid together with triethylamine, the most suitable amounts and ratios of formic acid to triethylamine have been described before, optimization needs to be performed by taking into account of the acidity of the source material compound and its stability toward the base and by further considering reactivity and selectivity.

According to the present invention, the reaction temperature can be broadly in the range from −20° C. to 100° C. When economic efficiency is taken into consideration, the reaction is performed in the vicinity of 25° C. to 40° C. room temperature. The most preferred temperature range is from 20° C. to 60° C. The reaction time differs according to the reaction conditions such as concentration of substrate, reaction temperature, and the substrate to catalyst molar ratio; however, the time until completion of the reaction can range from a few minutes to 100 hours.

The product may be refined by a known method such as column chromatography, distillation, recrystallization. In order to obtain optical alcohol, it is necessary that the chiral carbon atoms of two places in the metal complex catalysts represented by general formula (1) and general formula (2) of the present invention either both have an R configuration or both have an S configuration. By selecting either an R configuration or an S configuration it is possible to obtain the desired optical alcohol of an absolute configuration with a high enantioselectivity. Further, when the aim is the production of racemic alcohol, it is not necessary that the chiral carbon atoms thereof both have an R configuration or both have an S configuration, each carbon atom can independently have either configuration.

By the above method it is possible to obtain optically active cis-3-quinuclidinols having one or more substituted groups at the 2-position by reducing 3-quinuclidones having one or more substituted groups at the 2-position. According to the method described in the application for the present invention, any one of the optically active cis-3-quinuclidinols having $R^5$ at the 2-position represented by general formula (5) hereinafter or the optically active cis-3-quinuclidinols having $R^5$ at the 2-position represented by general formula (6) hereinafter can be produced with the 3-quinuclidinones having $R^5$ at the 2-position represented by general formula (3) hereinafter or the 3-quinuclidinones having $R^5$ at the 2-position represented by general formula (4) hereinafter and a mixture, at any ratio, of the 3-quinuclidinones having $R^5$ at the 2-position represented by general formula (3) hereinafter and the 3-quinuclidinones having $R^5$ at the 2-position represented by general formula (4) hereinafter. (Here $R^5$ is preferably diphenylmethyl group which may have one or more substituted groups, 3-pyridylmethyl group which may have one or more substituted groups, or benzyl group which may have one or more substituted groups.)

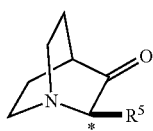

(3)

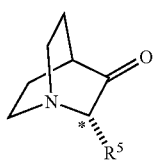

(4)

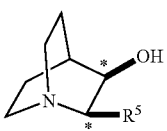

(5)

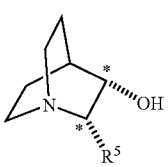

(6)

The reason for this is that, according to the present invention, in a system using the metal complex catalysts represented by general formula (1) or (2), in which it is possible to control the asymmetric points of two places because the 3-quinuclidinones having one or more substituted groups at the 2-position are subjected to asymmetric reduction, accompanied by dynamic kinetic resolution, there is the conventionally unheard-of advantage that optically active cis-quinuclidinols having one or more substituted groups at the 2-position can very efficiently be produced.

Depending on the substrate structure, minute amounts of optically active trans-3-quinuclidinols may be produced as a by-product of the method according to the present invention; however, optically pure cis-3-quinuclidinols having one or more substituted groups at the 2-position can be obtained from the optically active quinuclidinol produced in the reaction by a simple refining operation using a conventionally known method for increasing optical purity such as a suitable recrystallization or stereoastereomer method.

EXAMPLES

The reduction reaction of the 3-quinuclidinones having one or more substituted groups at 2-position in the present invention may be performed either by batch reaction or by continuous reaction. The invention will now be described in still greater detail by way of the Examples; however, the present invention is not limited to the Examples hereinafter. In the Examples, the reactions are all performed in an argon gas or nitrogen gas atmosphere. Dried and degassed solvents were used in the reaction.

The measurements hereinafter were performed with the following instruments:

NMR:

LA 400 (400 MHz) spectrometer
(manufactured by Nihon Denshi)
Internal standard substance: $^1$H-NMR . . . tetramethyxylane
External standard substance: $^{31}$P-NMR . . . 85% phosphoric acid
Optical purity: Gas chromatography Chirasil - DEX CB (0.25 mm × 25 m, DF = 0.25 µm)
(manufactured by Chrompack)
BETA DEX 120 (0.25 mm × 30 m, DF = 0.25 µm)
(manufactured by Supelco)
: High speed liquid chromatography
(manufactured by Shimazu Seisakusho)

Further, in the Examples, ee % represents an excessive enantiomer ratio and S/C represents the molar ratio of catalyst to substrate.

Example 1

Production of Optically Active cis-2-diphenylmethyl-3-quinuclidinol 0.511 g (1.75 mmol) of racemic 2-diphenylmethyl-3-quinuclidinone, 0.49 ml (3.51 mmol) of triethylamine, 0.33 ml (1.75 mmol) of formic acid (formic acid/triethylamine=5/2 to the substrate molar ratio), 5.5 mg (8.6×10$^{-3}$ mmol, S/C=200) of RuCl [(S,S)— TsDPEN] (p-cymene) were introduced into a 20 mL Schlenk flask under an argon atmosphere and stirred for 19 hours at 40° C. After making the reaction liquid basic by adding an aqueous solution of saturated sodium bicarbonate, the target substance was obtained with a yield of 86% by filtering the precipitated powder. By NMR spectroscopy it was confirmed that only 2-diphenylmethyl-3-quinuclidinol with the cis-configuration was obtained. The optical purity, determined by HPLC analysis (Daicel Chiralcel OD-H, Hexane/2-propanol/diethylamine=80/20/0.1, 0.5 mL/min., 25° C., the retention times of two types of optical isomers in the cis-configuration were 11.3 min. and 26.5 min.) was 99% ee; it was found that optically active cis-2-diphenylmethyl-3-quinuclidinol had been produced.

Example 2

Production of Optically Active cis-2-diphenylmethyl-3-quinuclidinol 0.511 g (1.75 mmol) of racemic 2-diphenylmethyl-3-quinuclidinone, 0.49 ml (3.51 mmol) of triethylamine, 0.33 ml (1.75 mmol) of formic acid (formic acid/triethylamine=5/2 to the substrate molar ratio), 5.5 mg ($8.6 \times 10^{-3}$ mmol, S/C=200) of RuCl [(S,S)-TsDPEN] (p-cymene) and, as solvent, 2 ml of N,N-dimethylformamide were introduced into a 20 mL Schlenk flask under an argon atmosphere and stirred for 19 hours at 40° C. After making the reaction liquid basic by adding an aqueous solution of saturated sodium bicarbonate, the target substance was obtained with a yield of 90% by filtering the precipitated powder. By NMR spectroscopy it was confirmed that only 2-diphenylmethyl-3-quinuclidinol with the cis-configuration was obtained. The optical purity was 99% ee.

Example 3

Production of Optically Active cis-2-diphenylmethyl-3-quinuclidinol

Except for using RuCl [(R,R)-TsDPEN (mesitylene), the reaction was performed under the same conditions as in Example 2; cis-2-diphenylmethyl-3-quinuclidinol with an optical purity of 95% ee was obtained with a yield of 43%.

Example 4

Synthesis of Optically Active 2-(3-pyridinylmethyl)-3-quinuclidinol 0.518 g (2.39 mmol) of racemic 2-(3-pyridinylmethyl)-3-quinuclidinone, 0.65 ml (4.66 mmol) of triethylamine, 0.44 ml (11.7 mmol) of formic acid (formic acid/triethylamine=5/2 to the substrate molar ratio), 5.5 mg ($8.6 \times 10^{-3}$ mmol, S/C=200) of RuCl [(S,S)— TsDPEN] (p-cymene) were introduced into a 20 mL Schlenk flask under an argon atmosphere and stirred for 19 hours at 40° C. The reaction liquid was diluted in dichloromethane, neutralized by potassium carbonate, and after removing the solids by filtration, the target substance was obtained with a yield of 49% by concentrating and drying to solids. By NMR spectroscopy it was confirmed that 2-(3-pyridinylmethyl)-3-quinuclidinol of only one of the diastereomers was obtained. The optical purity, determined by HPLC analysis (Daicel Chiralcel OD-H two columns connected in series, Hexane/2-propanol/diethylamine=80/20/0.1, 0.3 mL/min., 25° C., the retention times of the two types of optical isomers in the diastereomer obtained were 64.0 min. and 83.2 min.) was 85% ee.

Example 5

Synthesis of Optically Active 2-(3-pyridinylmethyl)-3-quinuclidinol

Except for using Cp*IrCl [(S,S)-TsDPEN], the reaction was performed under the same conditions as in Example 4; optically active 2-(3-pyridinylmethyl)-3-quinuclidinol was obtained as a single diastereomer with an optical purity of 71% ee and a yield of 100%.

Example 6

Synthesis of Optically Active 2-benzyl-3-quinuclidinol

Except for reacting racemic 2-benzyl-3-quinuclidinone, the reaction was performed under the same conditions as in Example 1; optically active 2-benzyl-3-quinuclidinol was obtained as a single diastereomer with an optical purity of 93% ee and a yield of 100%.

What is claimed:

1. A method for producing optically active 3-quinuclidinols having one or more substituted groups at the 2-position comprising reacting 3-quinuclidinones having one or more substituted groups at the 2-position with compounds selected from alcohol compounds having a hydrogen atom at the α-position, formic acid and formates in the presence of a metal complex represented by the general formula (1)

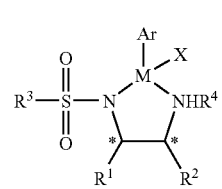

(1)

(wherein, $R^1$ and $R^2$ are both simultaneously or each independently alkyl groups, phenyl groups, naphthyl groups or cycloalkyl groups which may have one or more substituted groups, optionally, $R^1$ and $R^2$ may also join to form an alicyclic ring, $R^3$ is an alkyl group, perfluoroalkyl group, naphthyl group, phenyl group or camphor which may have one or more substituted groups, $R^4$ is a hydrogen atom or an alkyl group, Ar, joined to M via a π bond, is a benzene ring which may have one or more substituted groups or a cyclopentadienyl group which may have one or more substituted groups, X is a hydride group or an anionic group, M is ruthenium, rhodium or iridium, * represents an asymmetric carbon atom).

2. A method for producing optically active 3-quinuclidinols having one or more substituted groups at the 2-position comprising reacting 3-quinuclidinones having one or more substituted groups at the 2-position with compounds selected from alcohol compounds having a hydrogen atom at the α-position, formic acid and formates in the presence of a metal complex represented by the general formula (2)

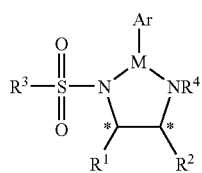

(2)

(wherein, $R^1$, $R^2$, $R^3$, $R^4$, Ar, M and * each have the same meaning as in claim 1).

3. A method according to claim 1 wherein, in general formula (1), M is ruthenium.

4. A method according to claim 1 wherein, in general formula (1), M is iridium.

5. A method according to claim 1 wherein, in general formula (1), M is rhodium.

6. A method according to claim 1 characterized in that the optically active 3-quinuclidinols having one or more substituted groups at the 2-position are obtained diastereoselectively and enantioselectively.

7. A method according to claim 1; wherein the 3-quinuclidinones having one or more substituted groups at the 2-position are the compounds expressed by general formula (3) hereinafter, the compounds expressed by general formula (4) hereinafter, or a mixture, at any ratio, of the compounds expressed by general formula (3) and the compounds expressed by general formula (4), and the optically active 3-quinuclidinols having one or more substituted groups at the 2-position that are to be produced are the optically active cis-3-quinuclidinols having $R^5$ at the 2-position represented by general formula (5) or general formula (6) hereinafter

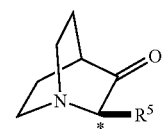

(3)

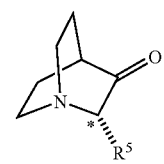

(4)

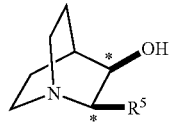

(5)

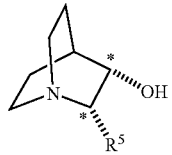

(6)

(wherein, $R^5$ represents an alkyl group with a carbon number of 1 to 20, which may be substituted by an aromatic ring and which may include a heteroatom, * represents an asymmetric carbon atom).

8. A method according to claim 7 wherein, in general formulae (3) to (6) according to claim 7, $R^5$ is a diphenylmethyl group, a 3-pyridylmethyl group or a benzyl group, which may have one or more substituted groups.

9. A method according to claim 2 wherein, in general formula (2), M is ruthenium.

10. A method according to claim 2 wherein, in general formula (2), M is iridium.

11. A method according to claim 2 wherein, in general formula (2), M is rhodium.

12. A method according to claim 2 characterized in that the optically active 3-quinuclidinols having one or more substituted groups at the 2-position are obtained diastereoselectively and enantioselectively.

13. A method according to claim 2; wherein the 3-quinuclidinones having one or more substituted groups at the 2-position are the compounds expressed by general formula (3) hereinafter, the compounds expressed by general formula (4) hereinafter, or a mixture, at any ratio, of the compounds expressed by general formula (3) and the compounds expressed by general formula (4), and the optically active 3-quinuclidinols having one or more substituted groups at the 2-position that are to be produced are the optically active cis-3-quinuclidinols having $R^5$ at the 2-position represented by general formula (5) or general formula (6) hereinafter

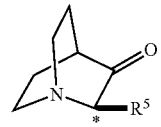

(3)

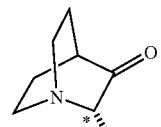

(4)

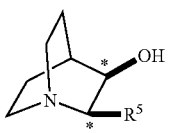

(5)

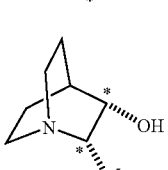

(6)

(wherein, $R^5$ represents an alkyl group with a carbon number of 1 to 20, which may be substituted by an aromatic ring and which may include a heteroatom, * represents an asymmetric carbon atom).

14. A method according to claim 13 wherein, in general formulae (3) to (6) according to claim 13, $R^5$ is a diphenylmethyl group, a 3-pyridylmethyl group or a benzyl group, which may have one or more substituted groups.

* * * * *